US00PP28220P3

(12) United States Plant Patent
Tufaro

(10) Patent No.: US PP28,220 P3
(45) Date of Patent: Jul. 25, 2017

(54) STRAWBERRY PLANT NAMED 'CHARLENE'

(50) Latin Name: *Fragaria×ananassa Duchesne*
Varietal Denomination: Charlene

(71) Applicant: Nova Siri Genetics S.R.L., Nova Siri (MT) (IT)

(72) Inventor: Nicola Tufaro, Nova Siri (IT)

(73) Assignee: Nova Siri Genetics S.R.L., Nova Siri (MT) (IT)

( * ) Notice: Subject to any disclaimer, the term of this patent is extended or adjusted under 35 U.S.C. 154(b) by 67 days.

(21) Appl. No.: 14/545,598

(22) Filed: May 28, 2015

(65) Prior Publication Data

US 2016/0029529 P1 Jan. 28, 2016

(30) Foreign Application Priority Data

Jul. 23, 2014 (QZ) ..... PBR 2014/1878

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Anne Grunberg
(74) *Attorney, Agent, or Firm* — Buchanan Ingersoll & Rooney PC

(57) ABSTRACT

A new and distinct short-day strawberry plant is provided. Attractive semi-early ripening substantially uniform medium red generally cordate fruit having a firm flesh is formed in good yield that is longer than broad in configuration. White inflorescence is formed on a semi-early basis that tends to be disposed above the foliage. A calyx commonly is displayed that is substantially equal to the diameter of the corolla when open. A semi-dense upright growth habit is displayed.

25 Drawing Sheets

Botanical/commercial classification: *Fragaria×ananassa* Duchesne/Strawberry Plant.

Varietal denomination: cv. Charlene.

BACKGROUND OF THE INVENTION

The new and distinct short-day strawberry plant variety of the present invention was the product of a controlled breeding program that was carried out at Nova Siri (MT) Italy located at 40° 08' 40" N-16° 39' 40" E and 10 meters above sea level. The female parent (i.e., the seed parent) was the 'Marisol' cultivar (U.S. Plant Pat. No. 25,637, filed Jul. 3, 2013, and European Application No. 2012/1377)), a short-day strawberry variety having attractive, semi-early ripening, bright red, primarily conical fruit having a firm flesh, substantially uniform medium red in color, and the ability to produce large fruits with high content of sugar, and presenting good tolerance to infection in plants by *Pytophthora Cactorum*; and the male parent (i.e., pollen parent) was the unreleased 'A050389' cultivar (non-patented in the United States), a short-day strawberry variety having very early-season ripening, good yield, and good tolerance to soils with a sodium content at what is generally considered the agronomic limit for sodium. The parentage of the new variety can be summarized as follows:

'Marisol'×'A050389'.

The seeds resulting from the pollination were sown and small plants were obtained which were physically different from each other. Selective study and testing resulted in the identification of a single plant of the new variety.

The new variety initially was designated EE-10-14.

It was found that the new short-day strawberry plant variety of the present invention displays the following combination of characteristics:

(a) exhibits a semi-dense upright globose growth habit,
(b) displays on a semi-early basis white inflorescence at a level generally above the foliage,
(c) commonly displays a calyx that is substantially equal to the diameter of the corolla when open, and
(d) forms in abundance attractive semi-early ripening large medium red generally cordate fruit having firm flesh that is longer than broad in configuration.

The new variety of the present invention can be readily distinguished from previously known strawberry cultivars including the 'Camarosa' cultivar (U.S. Plant Pat. No. 8,708), the female parent 'Marisol', and the male parent 'A050389', as indicated in detail hereafter. The comparative 'Camarosa' plants described herein were obtained commercially in Italy and Poland. The comparative 'Marisol' and 'A050389' plants were both owned by Nova Siri Genetics and come from their own collection.

The new cultivar possesses characteristics that commonly are sought by commercial strawberry growers. The substantially uniform attractive firm medium red semi-early ripening fruit is provided in good yields. Accordingly, the new cultivar is considered to be a promising new plant for commercial introduction.

The new cultivar requires an induction period for flowering. This can be achieved by growing in a colder climate away from the equator or at a higher altitude above sea level.

During observation to date, the fruit has shown mild sensitivity to Powdery Mildew attack after a rainy period.

The new cultivar has been asexually reproduced by the use of stolon's at Ochla, Poland located at 51° 848 N-15°

447 E and at Nova Siri (MT) Italy, and by in vitro tissue culture. No rooting problems were encountered. The combination of characteristics exhibited by the new plant has been found to be stable and is reliably transmitted to succeeding generations following such asexual reproduction. Accordingly, the new cultivar reproduces true-to-type manner by such asexual reproduction.

The new plant has been named 'Charlene'.

BRIEF DESCRIPTION OF THE PHOTOGRAPHS

The accompanying photographs show, as nearly true as it is reasonably possible to make the same in color illustrations of this character, typical specimens of the new cultivar as well as typical specimens of the 'Camarosa' cultivar (U.S. Plant Pat. No. 8,708), the female parent (i.e., the seed parent) 'Marisol' (U.S. Plant Pat. No. 25,637, filed Jul. 3, 2013, and European Application No. 2012/1377) and the male parent (i.e., pollen parent) 'A050389' plant (non-patented) for comparative purposes. The plants had been asexually reproduced from stolons and were planted under the cover of plastic tunnels during mid-October 2013 at Nova Siri (MT), Italy.

Figure 1:
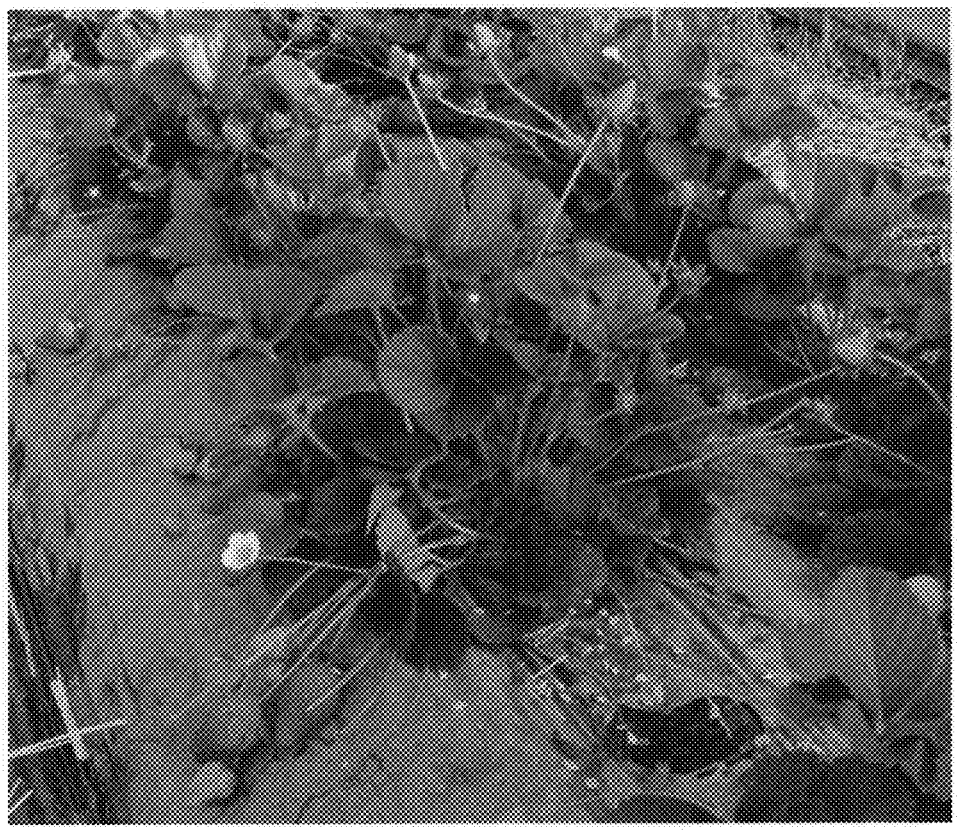
FIG. 1 shows an upright flowering plant of the new cultivar on Mar. 20, 2014 where the newly formed flowers commonly are disposed above medium dense foliage.
Figure 2:
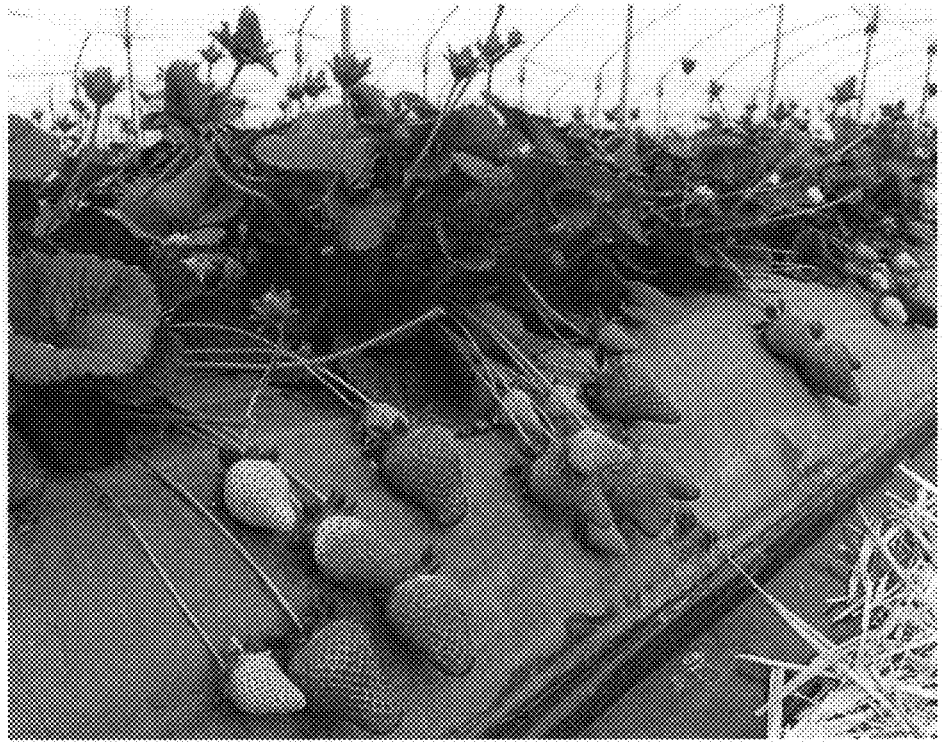
FIG. 2 shows a row of fruiting plants of the new variety on Feb. 14, 2014 wherein abundant substantially uniform fruit production is apparent.
Figure 3:
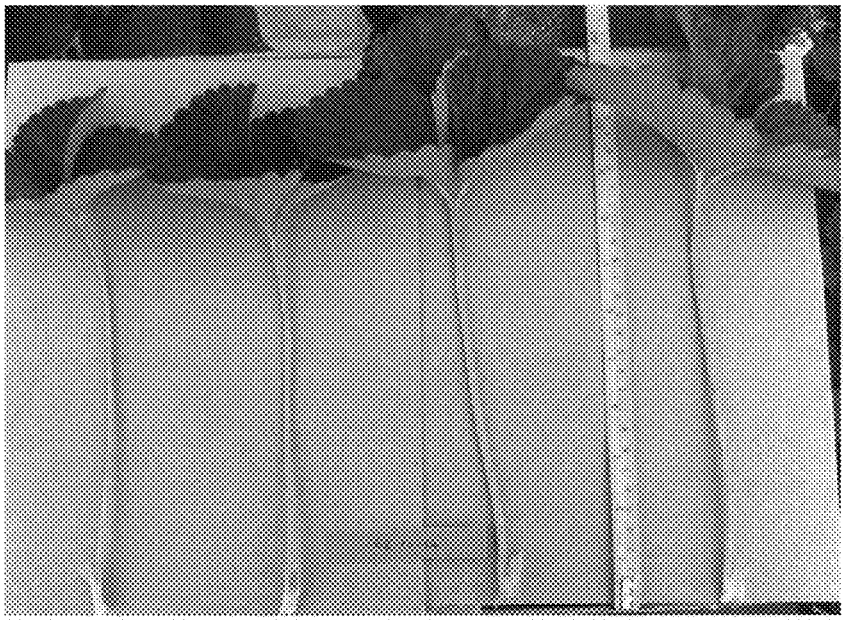
FIG. 3 shows typical three-leaflet leaves of the new cultivar including petioles and stipules. Dimensions in centimeters are included at the right for comparative purposes.
Figure 4:
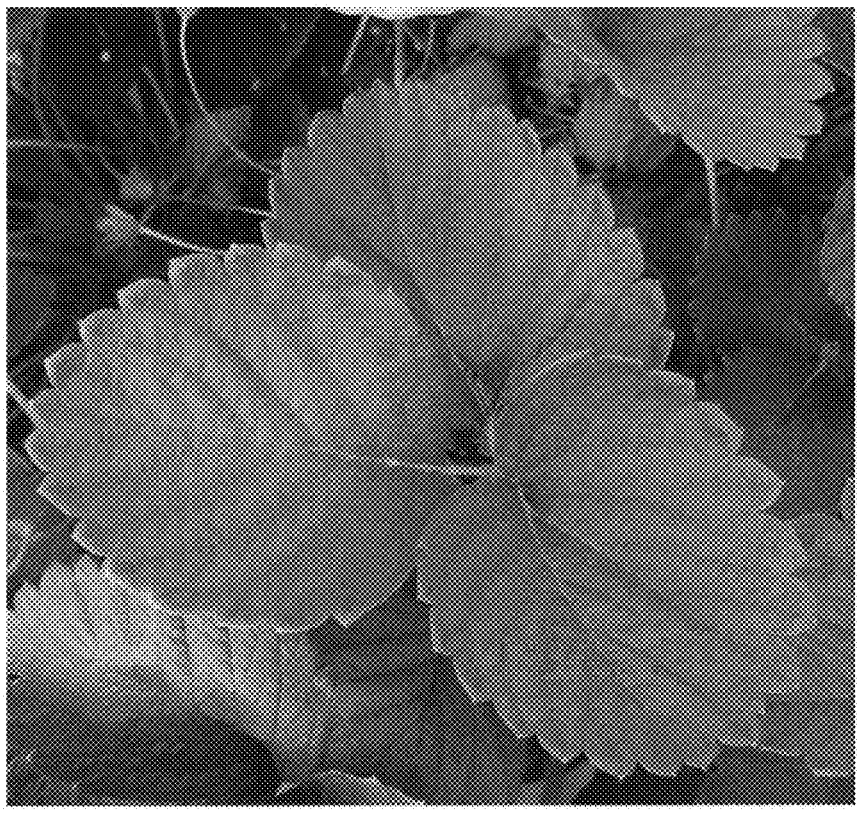
FIG. 4 shows from above the upper surface of a typical three-leaflet leaf of the new cultivar.
Figure 5:
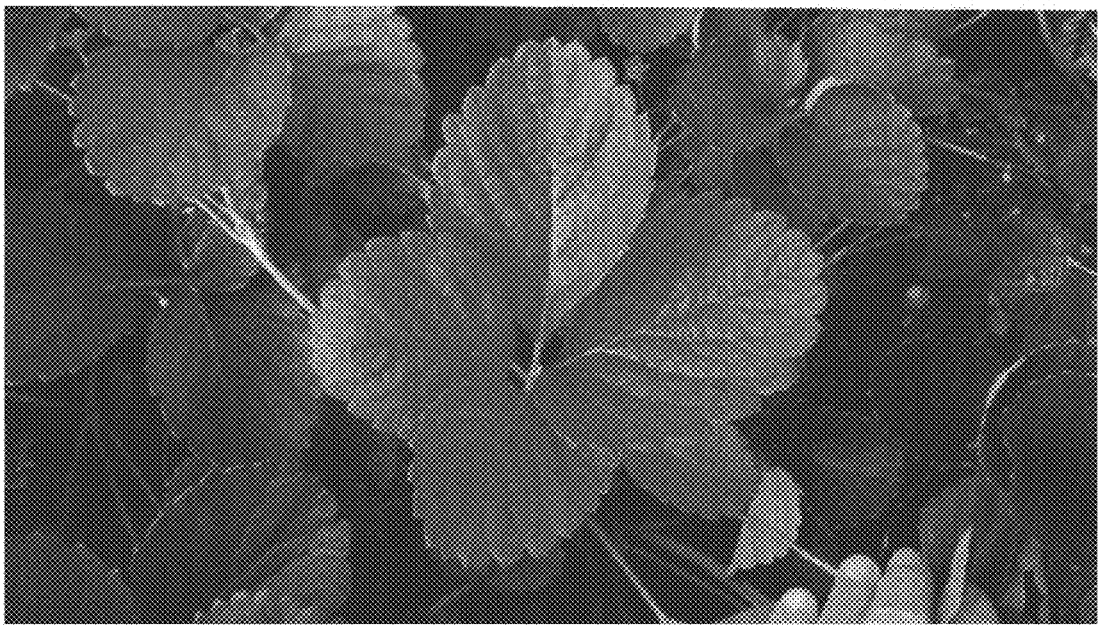
FIG. 5 shows from above a typical four-leaflet leaf of the new cultivar.
Figure 6:
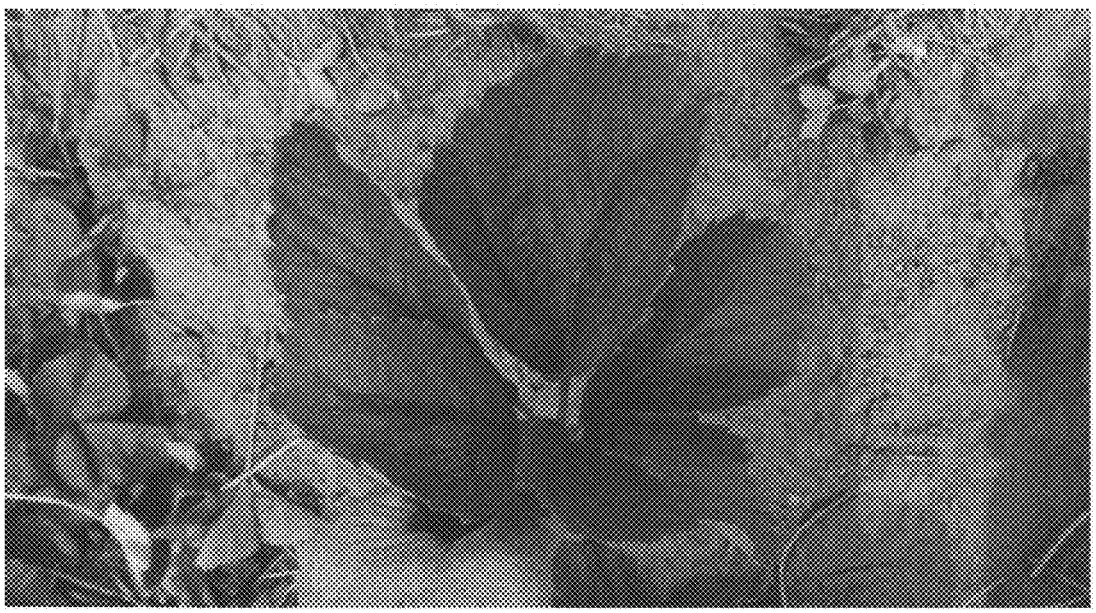
FIG. 6 shows from above a typical five-leaflet leaf that is occasionally displayed by the new cultivar.
Figure 7:
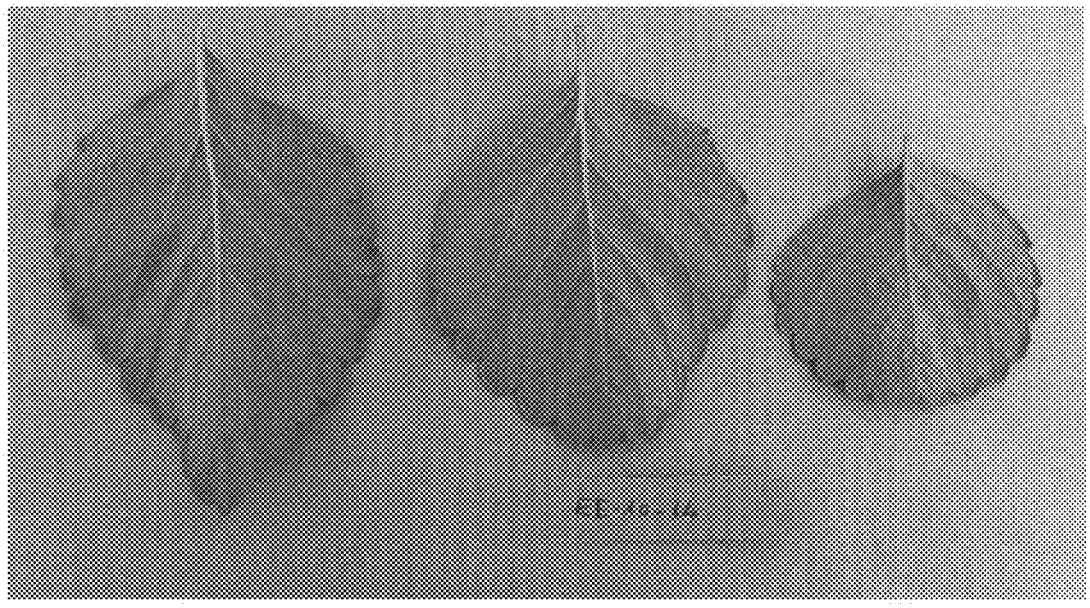
FIG. 7 shows the under surfaces of typical terminal leaflets of varied sizes of the new cultivar.
Figure 8:
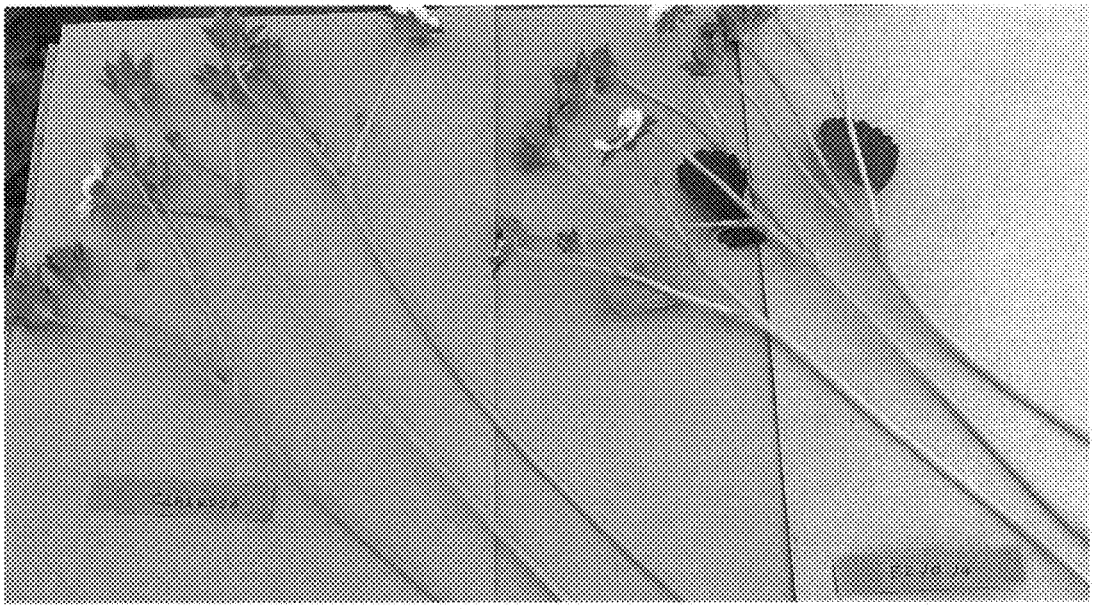

FIG. 8 shows for comparative purposes at the right typical inflorescence of the new cultivar which commonly also bear a single leaflet, and at the left typical inflorescence of the 'Camarosa' cultivar (U.S. Plant Pat. No. 8,708) where a single leaflet is absent.

Figures 9, 10:
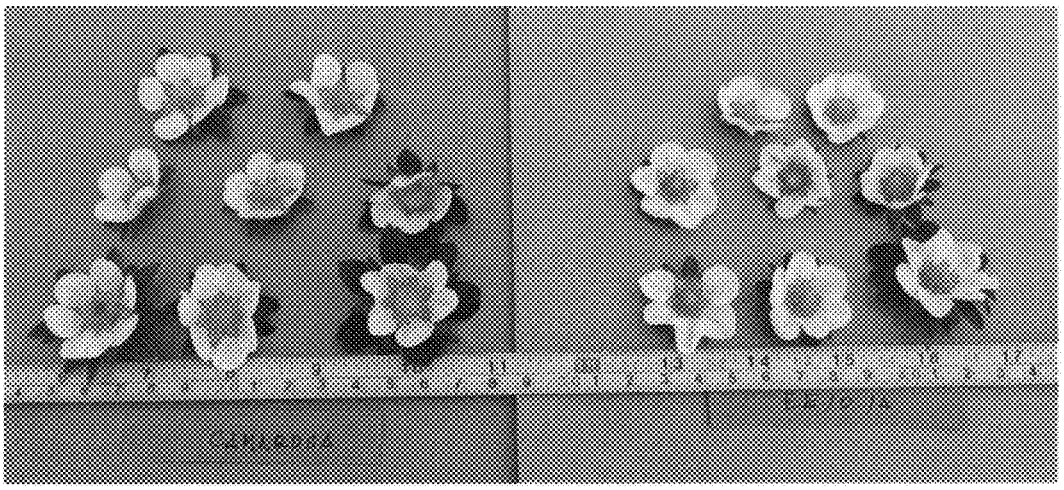

FIG. 9 shows from above for comparative purposes typical flowers of the 'Camarosa' cultivar (U.S. Plant Pat. No. 8,708) wherein the diameter of open calyx commonly exceeds that of the open corolla. Dimensions in centimeters and inches are included for comparative purposes.

FIG. 10 shows from above typical flowers of the new cultivar wherein the diameter of the open calyx is substantially equal to the diameter of the open corolla. Dimensions in centimeters and inches are included for comparative purposes.

Figures 11, 12:
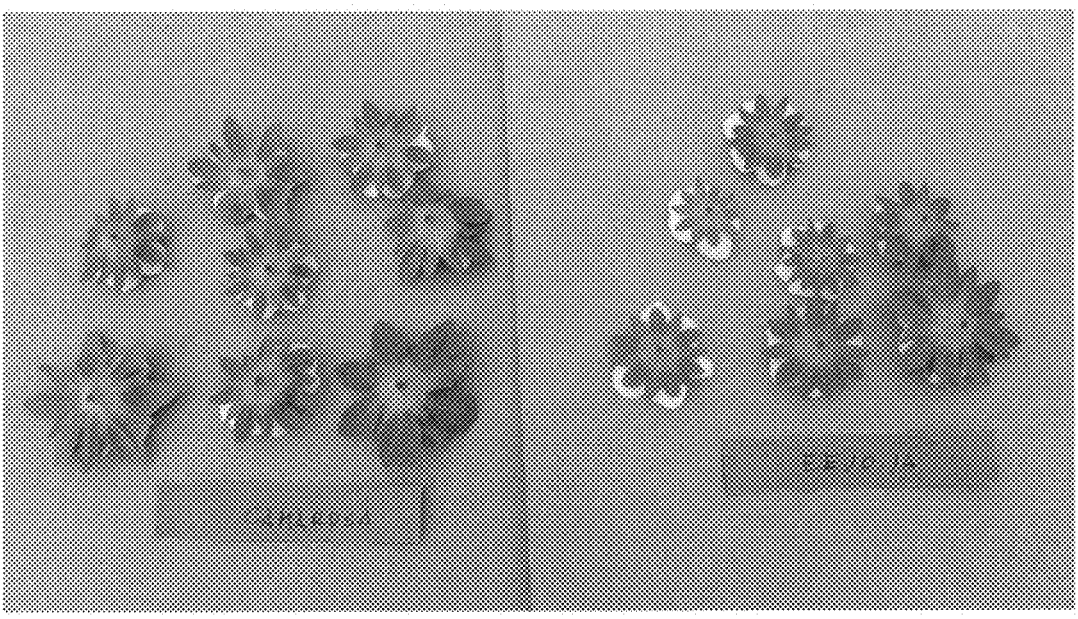

FIG. 11 shows from below for comparative purposes typical flowers of the 'Camarosa' cultivar (U.S. Plant Pat. No. 8,708). Unlike the new cultivar, it is observed that the depicted open calyx commonly extends beyond the diameter of the open corolla.

FIG. 12 shows from below typical flowers of the new cultivar wherein the diameter of the open calyx commonly is substantially equal to the diameter of the corolla when open.

Figures 13, 14:
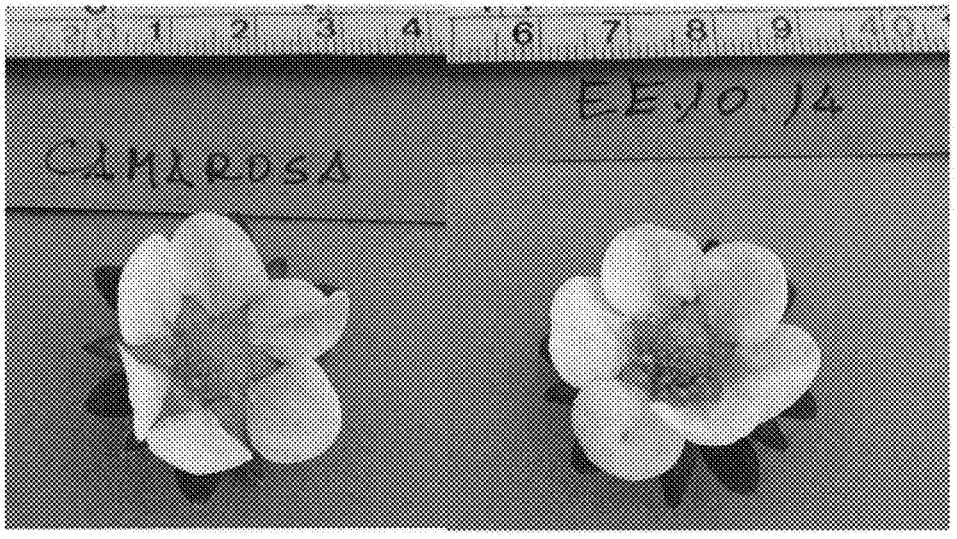

FIG. 13 shows from above for comparative purposes a typical flower of the 'Camarosa' cultivar (U.S. Plant Pat. No. 8,708) wherein the petals commonly are approximately equal in length and breadth. Dimensions in centimeters are included at the top.

FIG. 14 shows from above a typical flower of the new cultivar wherein the petals tend to be slightly broader than long. Dimensions in centimeters are included at the top.

Figure 15:
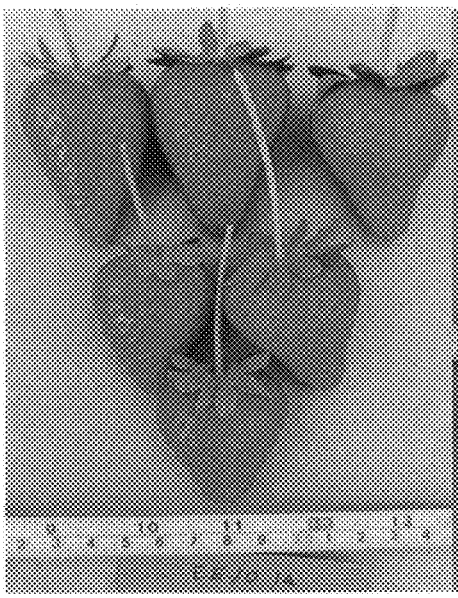

FIG. 15 shows typical attractive whole substantially uniform cordate fruit of the new cultivar wherein the sepals of the calyx tend to extend substantially horizontally outwards. Dimensions in centimeters and inches are included at the bottom for comparative purposes.

Figure 16:
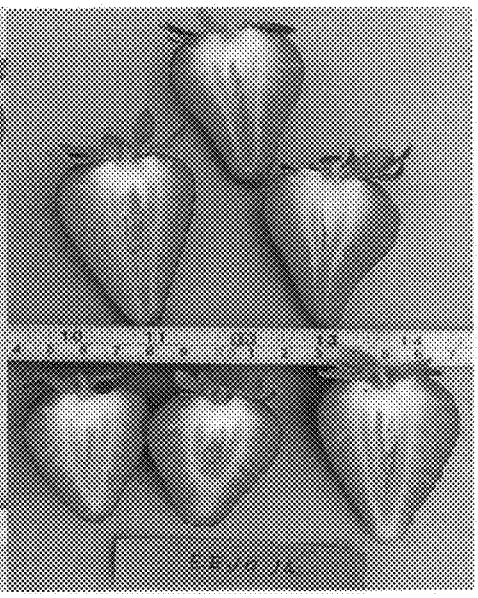

FIG. 16 shows typical sections showing the interior of the fruit of the new cultivar. Dimensions in centimeters and inches are included for comparative purposes.

Figure 17:
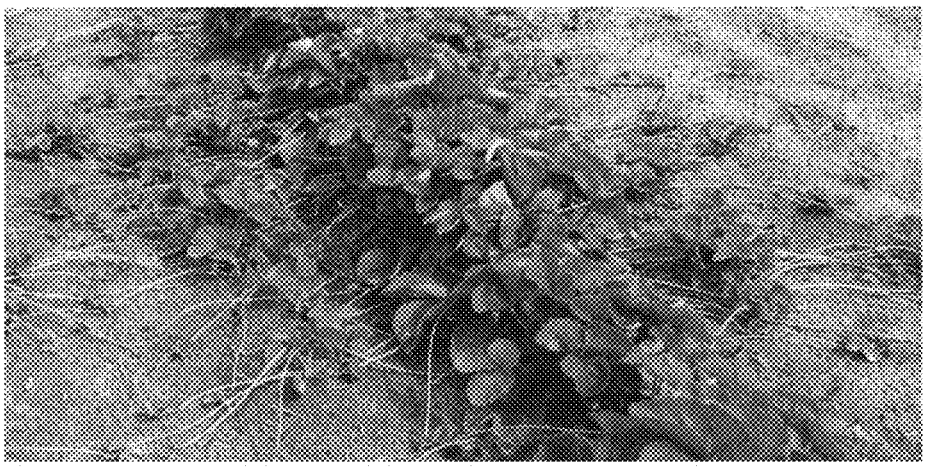

FIG. 17 shows on Jul. 30, 2013 typical plants of the new cultivar wherein the tendency to form stolons in a medium-to-high quantity is illustrated.

Figure 18:
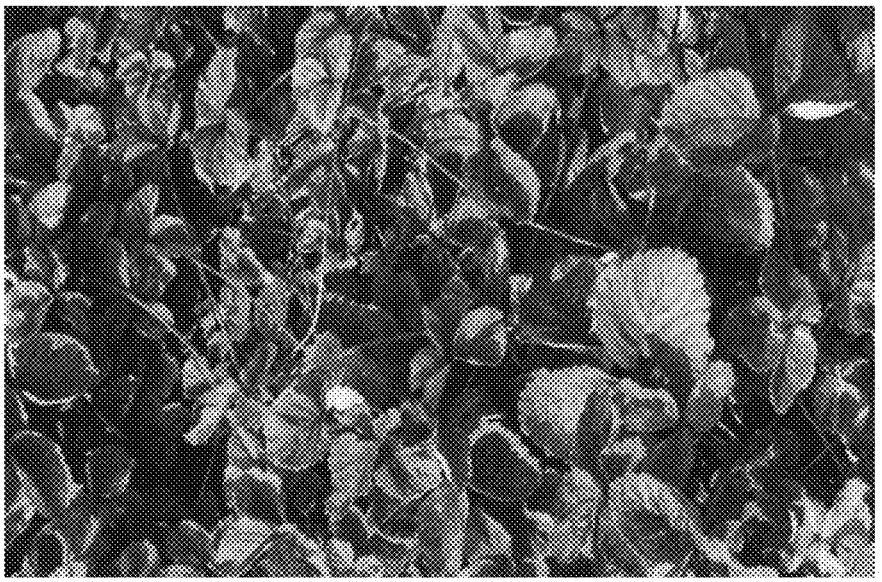

FIG. 18 shows during November 2014 typical plants of the new cultivar wherein anthocyanin coloration of the stolons is readily apparent.

Figure 19:
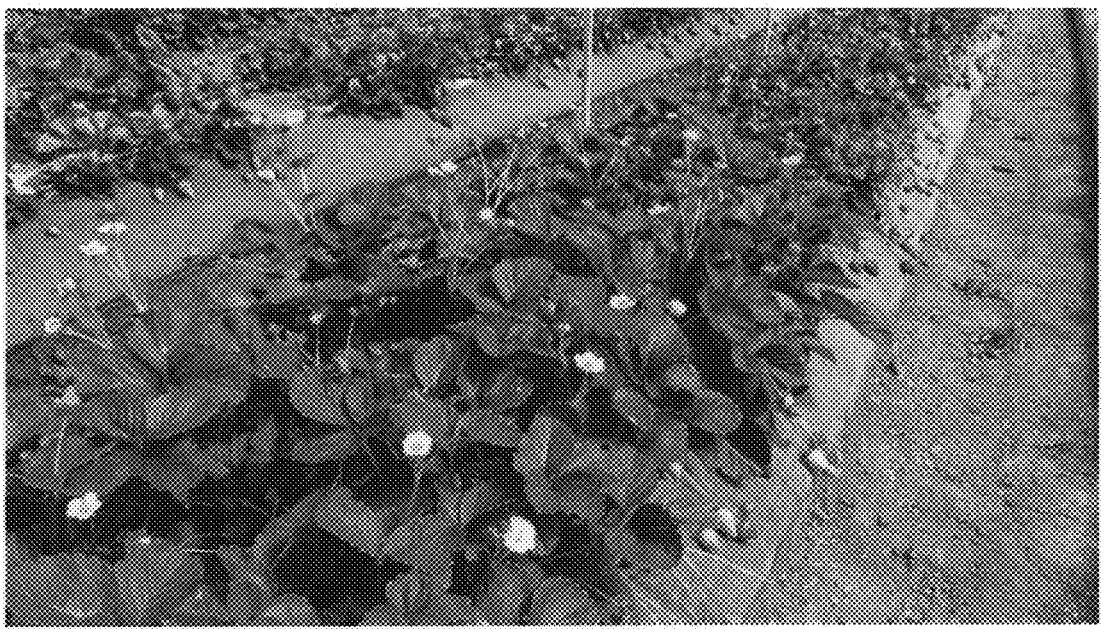

FIG. 19 shows on Apr. 29, 2014 a row of mature fruiting plants of the new cultivar wherein the inflorescence is shown to be disposed above the foliage.

Figure 20:
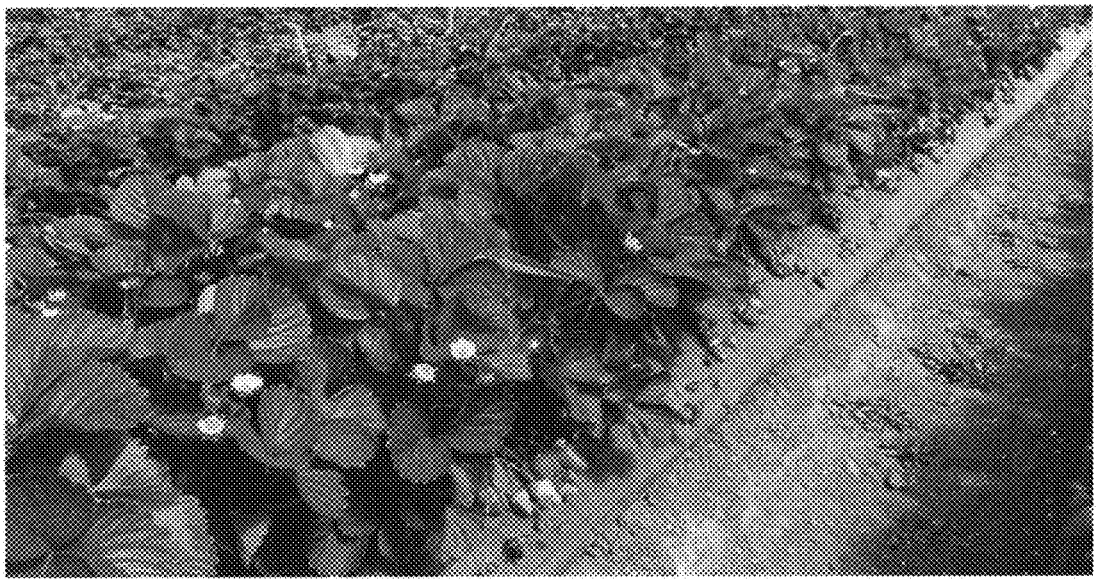

FIG. 20 shows for comparative purposes on Apr. 29, 2014 a row of mature fruiting plants of the 'Camarosa' cultivar (U.S. Plant Pat. No. 8,708) wherein the inflorescence is shown to be disposed at substantially the same level as the foliage. When compared to FIG. 19, it is seen that the foliage of the 'Camarosa' cultivar tends to be somewhat denser than that of the new cultivar, and the foliage coloration is of the new cultivar is somewhat darker than that of the 'Camarosa' cultivar.

Figure 21:
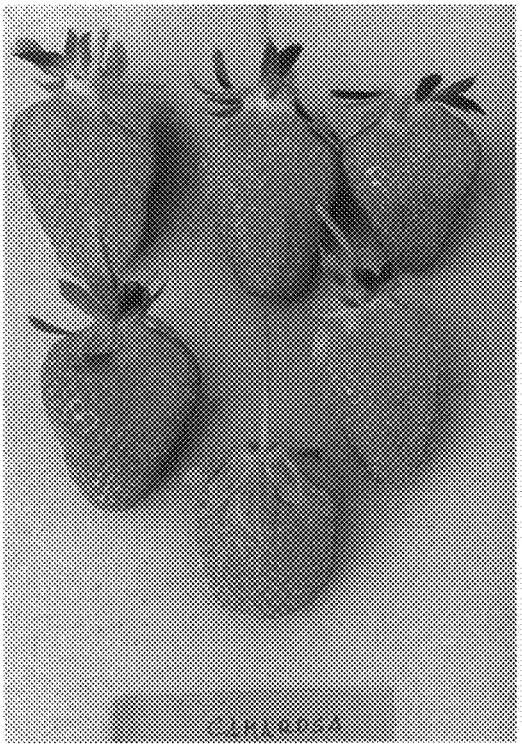

FIG. 21 shows typical whole fruit of the 'Camarosa' cultivar (U.S. Plant Pat. No. 8,708) wherein the fruit is raised at the top end where the calyx is attached.

Figure 22:
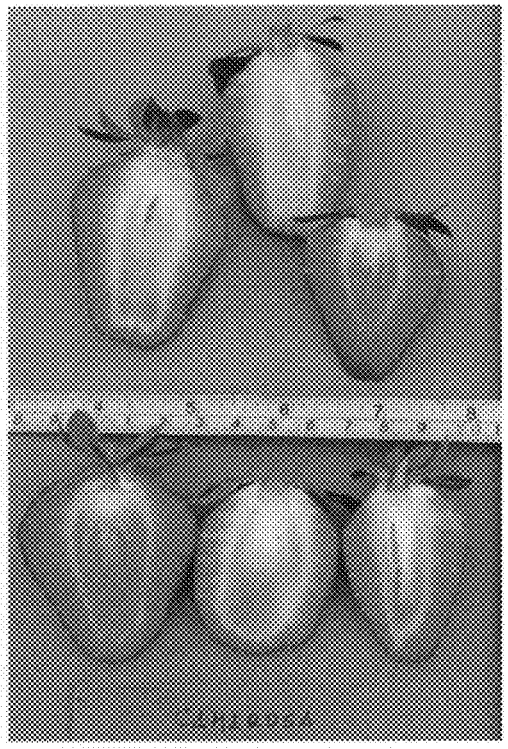

FIG. 22 shows typical fruit sections of the 'Camarosa' cultivar (U.S. Plant Pat. No. 8,708) wherein it is further apparent that unlike the new cultivar the fruit is raised at the top portion where the calyx is attached. Also, it is noted that the fruit of the 'Camarosa' cultivar generally tends to be less uniform in configuration than that of the new cultivar and to be more rhomboid to cylindrical in configuration. Dimensions in centimeters and inches are included for comparative purposes.

Figure 23:
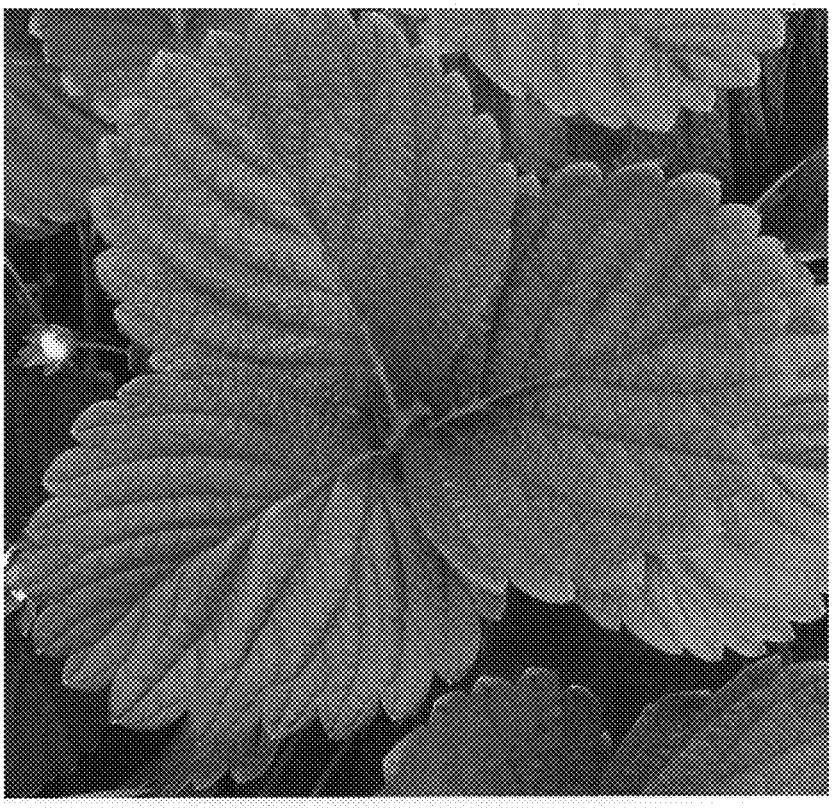

FIG. 23 shows for comparative purposes a typical three-leaflet leaf of the 'Camarosa' cultivar wherein the terminal leaflet tends to be substantially as long as broad unlike the new cultivar where the terminal leaflet commonly tends to be longer than broad. Also, blistering on the upper surfaces of the leaflets the 'Camarosa' cultivar commonly tends to be stronger than that displayed by the new cultivar.

Figure 24:
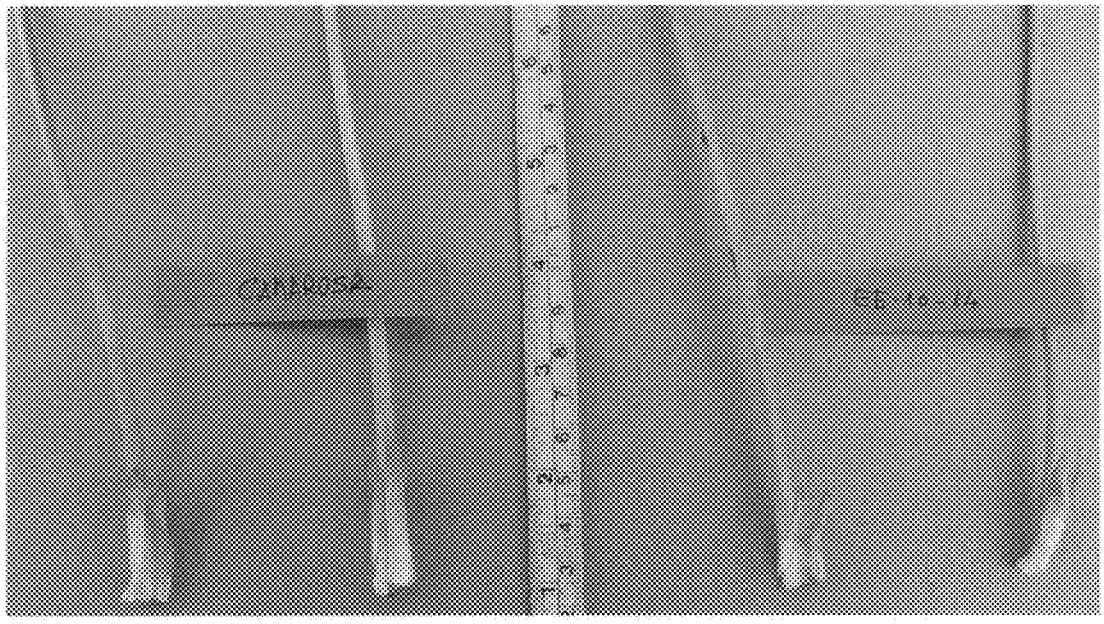

FIG. 24 shows for comparative purposes typical petioles of the new cultivar on the right and typical petioles of the 'Camarosa' cultivar on the left. Anthocyanin coloration on the stipules of the 'Camarosa' cultivar is absent and on the new cultivar is present and weak. Dimensions in centimeters and inches are included at the center.

Figure 25:
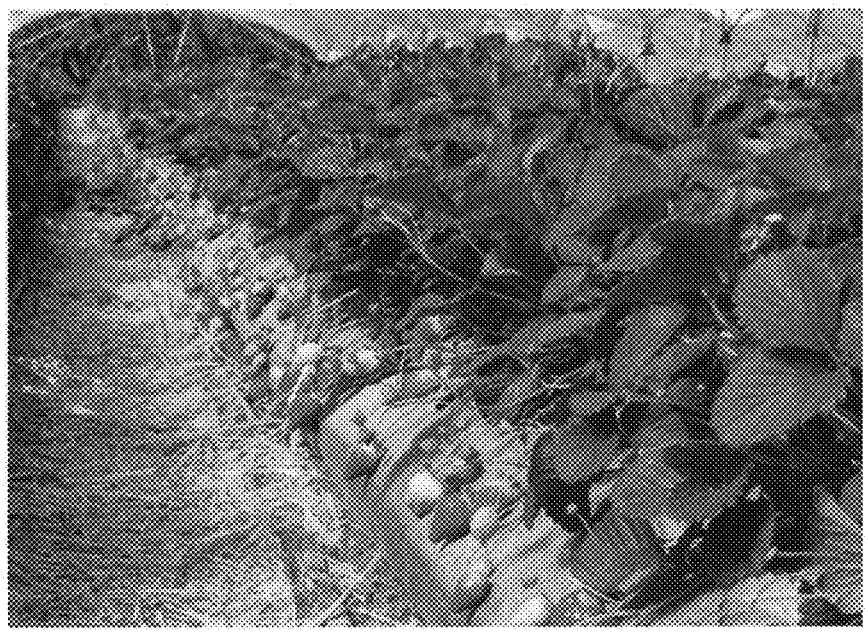

FIG. 25 shows for comparative purposes a row of flowering and fruiting plants of the female parent variety ('Marisol') where the flowers commonly are disposed slightly above the foliage. In the new variety, the flowers are disposed well above the foliage (see, e.g., FIG. 19).

Figure 26:
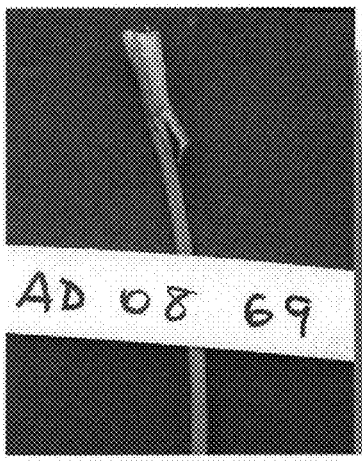
Figure 27:
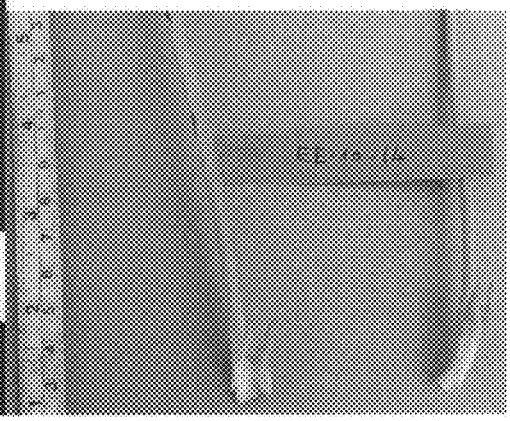

FIGS. 26 and 27 show for comparative purposes a typical petiole of the female parent variety ('Marisol'; identified in some of the figures as "AD 08 69") commonly approximately 19 to 24 cm in length on average and near Green Group 142A to 142B. In contrast, a typical petiole of the new variety (identified in some of the figures as "EE-10-14") is approximately 17 to 20 cm in length on average and near Yellow-Green Group N144C to Yellow Green Group N144D in color. Anthocyanin coloration of the stipule of 'Marisol' is present, and commonly bear some coloration of near Red Purple Group 65B to 65C. In contrast, in the stipules of the new variety, anthocyanin coloration is very weak of near Red-Purple Group 69C to near Red Purple Group 69D.

Figure 28:
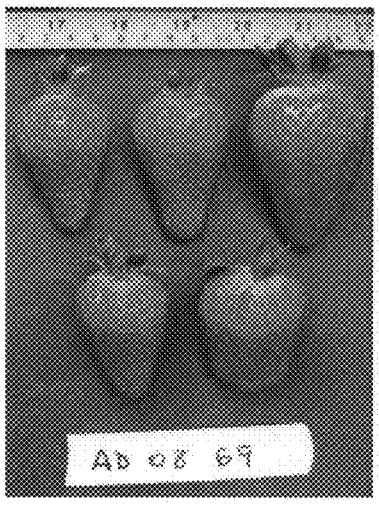

FIG. 28 shows for comparative purposes typical fruits of the female parent variety 'Marisol'. The 'Marisol' fruit is somewhat larger than fruit of the new variety, and the length: width ratio is larger in 'Marisol' in comparison to that of the new variety. Additionally, the disposition of the sepals of the calyx is generally upwards for the 'Marisol' variety, unlike the disposition of the sepals of the calyx for the new variety, which is generally outwards. The shape of fruits of the 'Marisol' variety is generally conical, unlike the shape of fruits of the new variety, which is cordate and moderately longer than broad. (see FIG. 15).

Figure 29:
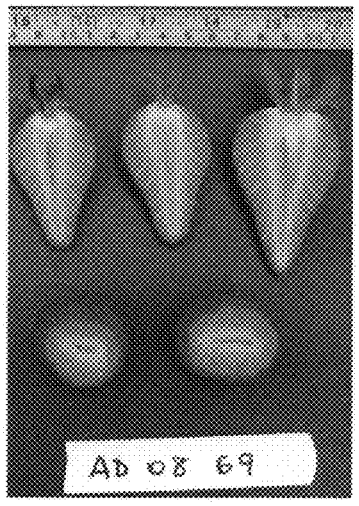

FIG. 29 shows for comparative purposes cross sections of typical fruits of the female parent variety 'Marisol'. External color in the 'Marisol' variety is substantially uniform and commonly near Red Group 42B to 42C. In contrast, external color in the new variety is substantially uniform and commonly near Red Group 45B to Red Group 46A. Internal color in fruits of variety 'Marisol' is commonly near Red Group 40A to 40B. In contrast, internal color in fruits of the new variety is commonly near Orange-Red Group 34A in the flesh with a core commonly near Orange-Red Group 34A to 34B in coloration.

Figure 30:
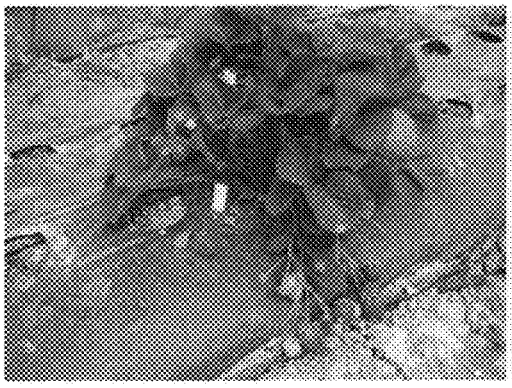
Figure 31:
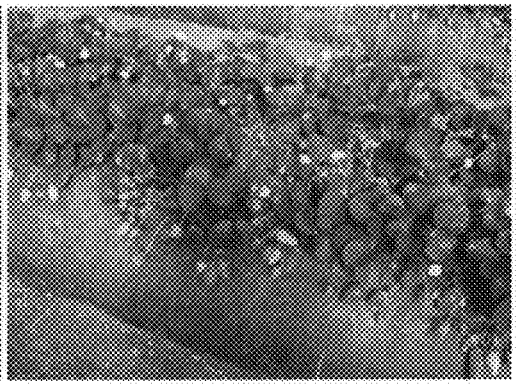

FIGS. 30 and 31 show for comparative purposes a plant and a row of flowering and fruiting plants of the male parent variety ('A050389') where the flowers commonly are disposed level with foliage. In the new variety, the flowers are disposed well above the foliage (see, e.g., FIG. 19).

Figure 32:
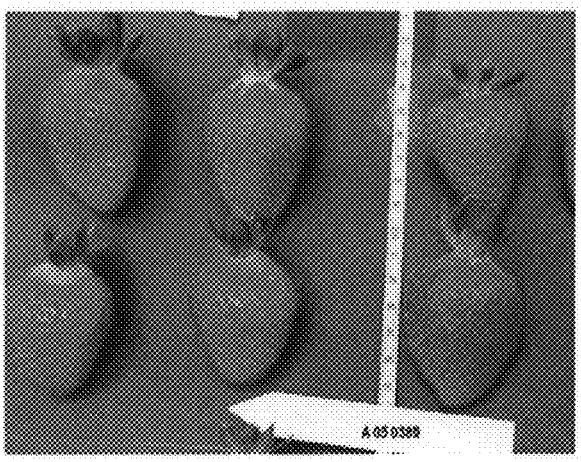
Figure 33:
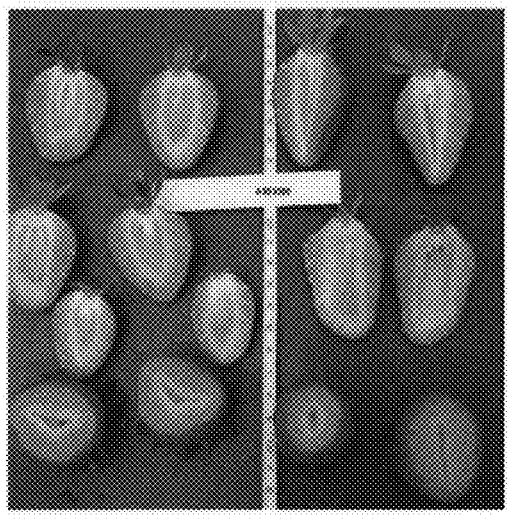

FIGS. 32 and 33 show for comparative purposes typical fruits of the male parent variety. The disposition of the sepals of the calyx is generally upwards for the male parent variety, unlike the disposition of the sepals of the calyx in the new variety, which is generally outwards. Shape of fruits of the male parent variety is generally rhomboid, unlike the shape of fruits of the new variety, which is generally cordate and moderately longer than broad. Additionally, the calyx attachment on the male parent variety is substantially raised, the disposition of the sepals of the calyx is generally upwards, and the calyx diameter (when open) is significantly smaller than the oveall fruit diameter commonly. In contrast, in the new variety, the calyx is substantially level at the point of attachment, the sepals are disposed generally outwards, and the calyx diameter (when open) is only slightly smaller than the overall fruit diameter. Further, shape and size of fruits on the male parent variety is highly variable, unlike on the new variety, in which the shape and size of fruits is highly uniform. (see, e.g., FIGS. 15 and 16)

Figure 34:
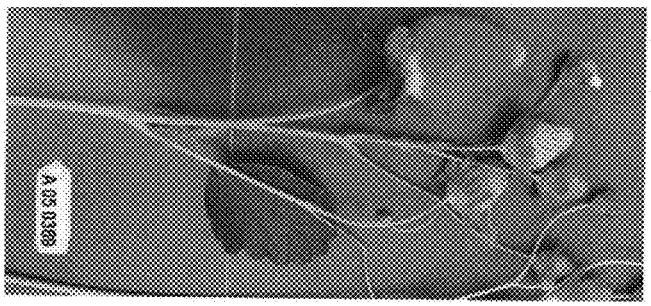

FIG. 34 shows for comparative purposes typical inflorescence of the male parent variety, which commonly bears 4 to 8 fruits per inflorescence. Further, in the male parent variety, there is significant difference in shape between primary and secondary fruits. In contrast, the new variety commonly has 1-4 fruits per inflorescence commonly with a very slight difference between terminal and other fruit (see, e.g., FIG. 8).

DETAILED BOTANICAL DESCRIPTION

The described plants had been asexually reproduced by the use of stolons and were growing under the cover of plastic tunnels at Nova Siri (MT) Italy and at Ochla, Poland. The chart used in the identification of color is The R.H.S. Colour Chart (Edition V) of The Royal Horticultural Society, London, England. Reference to common color terms is to be accorded ordinary dictionary significance.

Botanical class: *Fragaria×ananassa*, Duchesne, cv. 'Charlene'.

Plant:

*Type*.—Short-day.

*Configuration*.—Upright and semi-dense.

*Vigor*.—Medium.

*Leaves*.—Commonly approximately 25 to 33 cm in length on average including the petiole.

*Leaflets*.—Medium in size, commonly three or four (sometimes five) in number, approximately 5.5 to 6.5 cm in length on average for terminal leaflets and approximately 5 to 5.5 cm in width on average for terminal leaflets; the terminal leaflet tends to be longer in length than width, possesses a concave cross-section, possesses a serrate-to-crenate margin, and an obtuse to rounded base; blistering commonly is weak to medium in quantity; the glossiness on the upper surface is medium; and variegated coloration commonly is absent with the upper surface coloration commonly being near Green Group N137C to Green Group N139A and the under surface commonly being near Greyed-Green Group 191B to Greyed-Green Group 191C.

*Stolons*.—Medium in quantity, and commonly with some anthocyanin coloration of near Red-Purple Group 58B to Red-Purple Group 58C.

*Petioles*.—Commonly approximately 17 to 20 cm in length on average, near Yellow-Green Group N144C to Yellow-Green Group N144D in coloration, and commonly bear generally horizontally disposed fine pubescence.

*Stipules*.—Commonly approximately 2.2 to 2.5 cm in length, and commonly bear some very weak anthocyanin coloration of near Red-Purple Group 69C to near Red- Purple Group 69D. For the 'Camarosa' cultivar the stipules commonly are approximately 3.5 to 4.5 cm in length, bear no anthocyanin coloration, and commonly are near Green-Yellow Group 1B to Green-Yellow Group 1C in coloration.

Inflorescence:

*Flowering time*.—Medium.

*Flower disposition*.—Generally above the foliage.

*Flower number*.—Few to medium, commonly 1 to 4.

*Pedicel hairs*.—Pubescence generally disposed somewhat upwards.

*Pedicel color*.—Near Green Group 142B to near Yellow-Green Group 143C.

*Size*.—Large, with primary flowers commonly being approximately 2.3 to 3.1 cm in diameter on average, and secondary flowers commonly being approximately 2 to 2.4 cm in diameter on average, and commonly the calyx is substantially equal in diameter of the corolla when open.

*Petals*.—Overlapping, commonly number approximately 5 to 7 on average (typically 6), somewhat rounded overall, commonly the length is moderately shorter than the width, commonly approximately 0.8 to 1 cm in length on average, and approximately 1.1 to 1.3 cm in width on average, with a rounded apex, and near White Group N155A in coloration on the upper surface. For the 'Camarosa' cultivar the length and width of the petals tend to be substantially equal.

*Anthers*.—Commonly number approximately 21 to 26 on average, commonly disposed below the stamen, and near Yellow Group 6A to Yellow Group 6B in coloration. The new cultivar is self-fertile and pollen is formed in abundance.

*Sepals*.—Generally lanceolate in configuration, generally somewhat outwardly disposed, commonly number approximately 10 to 14 on average, commonly approximately 0.8 to 1.4 cm in length on average and approximately 2 to 6 mm in width on average at the broadest point, unlike the 'Camarosa' cultivar the diameter of the open calyx commonly is substantially the same as that of the corolla (as illustrated in FIGS. 9 and 10), and the coloration on the upper surface is commonly near Green Group 141B to Green Group 143A and on the lower surface is commonly near Yellow-Green Group 147B.

Fruit:

*Bearing*.—Non-remontant.

*Timing*.—Medium-fruiting commonly with approximately 28 to 32 days from first blooming to first fruit ripening.

*Shape*.—Generally cordate, moderately longer than broad, commonly with a slight difference between terminal and other fruit.

*Size*.—Medium to large, with the primary fruit commonly being approximately 5.8 to 6.2 cm in length on average and approximately 3.8 to 4.2 cm in width on average at the broadest point.

*Surface*.—Generally smooth with strong glossiness.

*External color*.—Substantially uniform medium red and commonly near Red Group 45B to Red Group 46A in coloration.

*Internal color*.—Flesh is medium red, and commonly near Orange-Red Group 34A, and the core commonly is medium red Orange-Red Group 34A to Orange-Red Group 34B.

*Firmness*.—Firm to very firm.

*Cavity*.—Small (as illustrated in FIG. 16).

*Achenes*.—Located generally below the fruit surface and cover nearly the entire fruit surface commonly with only a very narrow band (if any) where achenes are absent, and commonly near Yellow-Orange Group 23B in coloration.

*Calyx*.—Commonly the fruit is substantially level at the point of attachment, the calyx commonly attaches to the fruit with medium adherence, the sepals are disposed generally outwards, and the calyx diameter when open in relation to the fruit diameter commonly is slightly smaller.

*Peduncle*.—Very long, commonly approximately 30 to 40 cm in length on average for primary fruit, and commonly near Green Group 141B to Green Group 143A in coloration.

*Pedicel*.—Commonly with pubescence extending outwards, and near Green Group 142B to Yellow-Green Group 144C in coloration.

SUPPLEMENTAL COMPARATIVE DATA

Hereafter, additional comparative fruit data is provided for the new 'Charlene' cultivar and the "Camarosa" cultivar. The plants had been asexually reproduced by the use of stolons and were growing under the cover of plastic tunnels. The fruit was evaluated and compared on the dates indicated. Average data is presented.

Accumulated Production of First Quality Fruit (g/plant)

| Cultivar | February 30th | March 30th | April 30th | May 30th |
|---|---|---|---|---|
| 'Charlene' | 40 | 156 | 394 | 588 |
| 'Camarosa' | 69 | 177 | 359 | 587 |
| 'Marisol' | none | 51 | 421 | 751 |

Overall Comparison of Average Fruit Weight

| Cultivar | g/fruit |
|---|---|
| 'Charlene' | 22.31 |
| 'Camarosa' | 22.13 |
| 'Marisol' | 22.50 |

Average Fruit Weight on Specified Dates

| Cultivar | March 30th (grams) | April 30th (grams) | May 30th (grams) |
|---|---|---|---|
| 'Charlene' | 24.43 | 22.50 | 19.00 |
| 'Camarosa' | 23.43 | 22.75 | 19.80 |
| 'Marisol' | 36.47 | 36.01 | 22.23 |

Fruit Analysis

| | 'Charlene' | 'Camarosa' | 'Marisol' |
|---|---|---|---|
| Firmness (average)* | 0.74 | 0.74 | 0.66 |
| Dry Matter (%)** | 8.71 | 8.90 | 7.70 |
| pH (to 20°) | 3.88 | 3.60 | 3.80 |
| Acidity as Anhydride Citric (%) | 0.70 | 0.90 | 0.75 |
| Soluble Solids (% Brix) | 9.00 | 7.60 | 7.95 |
| Maturity Index*** | 12.85 | 8.44 | 10.60 |

*Resistance to penetration measured in kilograms using a Turoni (Italy) pentrometer (20 Kg × 0.01).
**Weight of residue from the titration of the fruit after drying at 103° C. until a constant weight is achieved.
***Relation between soluble solids and acidity as acetic anhydride.

Plants of the new 'Charlene' cultivar have not been observed under all possible environmental conditions to date. Accordingly, it is possible that the phenotypic expression may vary somewhat with changes in light intensity and duration, cultural practices, and other environmental conditions.

The invention claimed is:

1. A new and distinct short-day strawberry plant that exhibits the following combination of characteristics:

(a) exhibits a semi-dense upright globose growth habit, (b) displays on a semi-early basis white inflorescence at a level generally above the foliage, (c) commonly displays a calyx that is substantially equal to the diameter of the corolla when open, and (d) forms in abundance attractive semi-early ripening large medium red generally cordate fruit having firm flesh that is longer than broad in configuration;

substantially as illustrated and described.

* * * * *